US011466297B2

(12) United States Patent
Sun et al.

(10) Patent No.: US 11,466,297 B2
(45) Date of Patent: Oct. 11, 2022

(54) METHODS OF OIL PRODUCTION IN MICROORGANISMS

(71) Applicant: MARA RENEWABLES CORPORATION, Dartmouth (CA)

(72) Inventors: Zhiyong Sun, Dartmouth (CA); Roberto E. Armenta, Dartmouth (CA); Mercia Valentine, Dartmouth (CA)

(73) Assignee: Mara Renewables Corporation, Dartmouth (CA)

( * ) Notice: Subject to any disclaimer, the term of this patent is extended or adjusted under 35 U.S.C. 154(b) by 0 days.

(21) Appl. No.: 17/395,459

(22) Filed: Aug. 6, 2021

(65) Prior Publication Data

US 2021/0363554 A1  Nov. 25, 2021

Related U.S. Application Data

(62) Division of application No. 14/719,183, filed on May 21, 2015.

(60) Provisional application No. 62/001,912, filed on May 22, 2014.

(51) Int. Cl.
*C12P 7/6427* (2022.01)
*C12P 7/6463* (2022.01)
*C12P 7/6472* (2022.01)

(52) U.S. Cl.
CPC ........... *C12P 7/6427* (2013.01); *C12P 7/6463* (2013.01); *C12P 7/6472* (2013.01)

(58) Field of Classification Search
CPC ...... C12P 7/6427; C12P 7/6463; C12P 7/6472
USPC ....................................................... 435/134
See application file for complete search history.

(56) References Cited

U.S. PATENT DOCUMENTS

| 5,340,594 | A | 8/1994 | Barclay |
| 5,340,742 | A | 8/1994 | Barclay |
| 6,607,900 | B2 | 8/2003 | Bailey et al. |
| 8,163,515 | B2 | 4/2012 | Burja et al. |
| 2005/0112736 | A1 | 5/2005 | Behrens et al. |
| 2009/0117194 | A1 | 5/2009 | Burja et al. |
| 2012/0202242 | A1 | 8/2012 | Hazlebeck et al. |
| 2012/0244584 | A1* | 9/2012 | Zhang ............... C12N 15/01 435/134 |

FOREIGN PATENT DOCUMENTS

| AU | 2004287953 | 5/2005 |
| CN | 1977038 | 6/2007 |
| CN | 101389749 | 3/2009 |
| EP | 1359224 | 11/2003 |
| EP | 2194138 | 6/2010 |
| WO | 2005021735 | 3/2005 |
| WO | 2005045003 | 5/2005 |
| WO | 2005045050 | 5/2005 |
| WO | 2007069078 | 6/2007 |
| WO | 2014141098 | 9/2014 |
| WO | 2015177641 | 11/2015 |
| WO | 2015177641 | 1/2016 |

OTHER PUBLICATIONS

U.S. Appl. No. 14/719,183 , Advisory Action, dated Aug. 15, 2018, 3 pages.
U.S. Appl. No. 14/719,183 , Advisory Action, dated Aug. 15, 2019, 3 pages.
U.S. Appl. No. 14/719,183 , Advisory Action, dated Oct. 16, 2019, 3 pages.
U.S. Appl. No. 14/719,183 , Final Office Action, dated Jul. 28, 2020, 17 pages.
U.S. Appl. No. 14/719,183 , Final Office Action, dated Mar. 9, 2018, 8 pages.
U.S. Appl. No. 14/719,183 , Final Office Action, dated May 1, 2019, 9 pages.
U.S. Appl. No. 14/719,183 , Non Final Office Action, dated Oct. 18, 2018, 7 pages.
U.S. Appl. No. 14/719,183 , Non-Final Office Action, dated Apr. 14, 2021, 12 pages.
U.S. Appl. No. 14/719,183 , Non-Final Office Action, dated Feb. 6, 2020, 15 pages.
U.S. Appl. No. 14/719,183 , Non-Final Office Action, dated Aug. 23, 2017, 5 pages.
U.S. Appl. No. 14/719,183 , "Restriction Requirement", dated Feb. 28, 2017, 5 pages.
AU2015263044 , "First Examination Report", dated Jul. 16, 2020, 7 pages.
AU2015263044 , "Second Examination Report", dated Oct. 22, 2020, 3 pages.
Burja et al., "Isolation and Characterization of Polyunsaturated Fatty Acid Producing Thraustochytrium Species: Screening of Strains and Optimization of Omega-3 Production", Applied Microbiology and Biotechnology, vol. 72, No. 6, Apr. 20, 2006, pp. 1161-1169.

(Continued)

*Primary Examiner* — Jennifer M. H. Tichy
(74) *Attorney, Agent, or Firm* — Kilpatrick Townsend & Stockton

(57) ABSTRACT

Provided herein are methods for producing one or more polyunsaturated fatty acids. The methods include the steps of providing a microorganism capable of producing polyunsaturated fatty acids, providing a medium comprising a high concentration of one or more carbon sources, low pH, or both, and culturing the microorganism in the medium under sufficient conditions to produce the one or more polyunsaturated fatty acids. Also provided are methods of culturing one or more microorganisms. The methods include culturing the microorganisms in a medium comprising a first amount of one or more carbon sources at a first concentration level, monitoring a carbon source concentration until the carbon source concentration is reduced below the first concentration level, and adding to the medium a second amount of one or more carbon sources to increase the carbon source concentration to a second concentration level.

10 Claims, 6 Drawing Sheets

Specification includes a Sequence Listing.

(56) References Cited

OTHER PUBLICATIONS

Application No. CA2,953,060, Office Action, dated Mar. 12, 2021, 4 pages.
Application No. CA2,953,060, Office Action, dated Feb. 20, 2020, 6 pages.
Chang et al., "Improvement of Docosahexaenoic Acid Production on Glycerol by Schizochytrium Sp. S31 with Constantly High Oxygen Transfer Coefficient", Bioresource Technology, vol. 142, 2013, pp. 400-406.
Application No. CN201580038746.4, Office Action, dated Sep. 1, 2020, 13 pages.
Application No. CN201580038746.4, Office Action, dated Jan. 6, 2020, 15 pages.
Application No. CN201580038746.4, Office Action, dated Jan. 6, 2021, 8 pages.
Application No. EP15795730.9, Extended European Search Report, dated Nov. 17, 2017, 9 pages.
Ganuza et al., "High-Cell-Density Caultivation of Schizochytrium Sp. In an Ammonium/Ph-Auxostat Fed-Batch System", Biotechnol Lett, vol. 30, No. 9, 2008, pp. 1559-1564.
Application No. IL249638, Office Action, dated Dec. 23, 2018, 6 pages.
Application No. IL249638, Office Action, dated Mar. 10, 2020, 6 pages.
IN201617043510, "First Examination Report", dated Jan. 31, 2020, 5 pages.
Application No. KR2016-7035946, Office Action, dated Aug. 24, 2020, 20 pages.
Application No. PCT/IB2015/001407, International Preliminary Report on Patentability, dated Dec. 1, 2016, 7 pages.
Application No. PCT/IB2015/001407, International Search Report and Written Opinion, dated Nov. 25, 2015, 9 pages.
Qu et al., "Batch, Fed-Batch and Repeated Fed-Batch Fermentation Processes of the Marine Thraustochytrid Schizochytrium Sp. For Producing Docosahexaenoic Acid", Bioprocess and Biosystems Engineering, vol. 36, No. 12, May 15, 2013, pp. 1905-1912.
Ren et al., "Regulation of Docosahexaenoic Acid Production by Schizochytrium Sp.: Effect of Nitrogen Addition", Bioprocess and Biosystems Engineering, vol. 37, Sep. 21, 2013, pp. 865-872.
Wong et al., "Docosahexaenoic acid production and ultrastructure of the thraustochytrid Aurantiochytrium mangrovei MP2 under high glucose concentrations," Mycoscience, 49:266-70 (2008).
Yokochi et al., "Optimization of docohexaenoic acid production by Schizochytrium limacinum SR21" Appl. Microbiol. Biotechnol. 29:72-76 (1998).

* cited by examiner

METHODS OF OIL PRODUCTION IN MICROORGANISMS

CROSS-REFERENCE TO RELATED APPLICATION

This application is a divisional of U.S. patent application Ser. No. 14/719,183, filed May 21, 2015, which claims priority to U.S. Provisional Application No. 62/001,912, filed May 22, 2014, which is incorporated herein by reference in its entirety.

BACKGROUND

In the field of oil production via fermentation of eukaryotic microorganisms, certain strategies have been established and widely accepted. One such strategy to avoid nutrient inhibition and to achieve high cell concentration is using fed-batch fermentation, in which the main substrates (mainly the carbon sources) are added in increments to maintain a continuous supply while avoiding high concentrations of the substrates in the fermentation medium. However, fed-batch fermentation usually requires careful planning of the substrate feeding regime and intensive real-time fermentation monitoring and control, which demands extensive man power and may lead to a high failure rate of the fermentation operation.

Another significant cost related to fermentation on an industrial scale includes procedures related to sterilization. These costs include expensive pressure vessel fermenters and steam-in-place systems as well as the associated operating costs for generating the steam.

SUMMARY

Provided herein are methods for producing one or more polyunsaturated fatty acids. The methods include the steps of providing a microorganism capable of producing polyunsaturated fatty acids, providing a medium comprising a high concentration of one or more carbon sources, low pH, or both, and culturing the microorganism in the medium under sufficient conditions to produce the one or more polyunsaturated fatty acids.

Also provided are methods of reducing contamination of a non-sterile culture of one or more microorganisms. The methods include culturing the microorganisms (i) in the presence of a high concentration of one or more carbon sources, (ii) under conditions of low pH, or (iii) a combination thereof, wherein the culturing reduces contamination of the non-sterile culture comprising the microorganisms.

Provided are methods of culturing one or more microorganisms. The methods include culturing the microorganisms in a medium comprising a first amount of one or more carbon sources at a first concentration level, monitoring a carbon source concentration until the carbon source concentration is reduced below the first concentration level, and adding to the medium a second amount of one or more carbon sources to increase the carbon source concentration to a second concentration level.

BRIEF DESCRIPTION OF THE DRAWINGS

FIG. 6 and FIG. 3 show data from the same 30 L fermentation.

DETAILED DESCRIPTION

Figure 1:
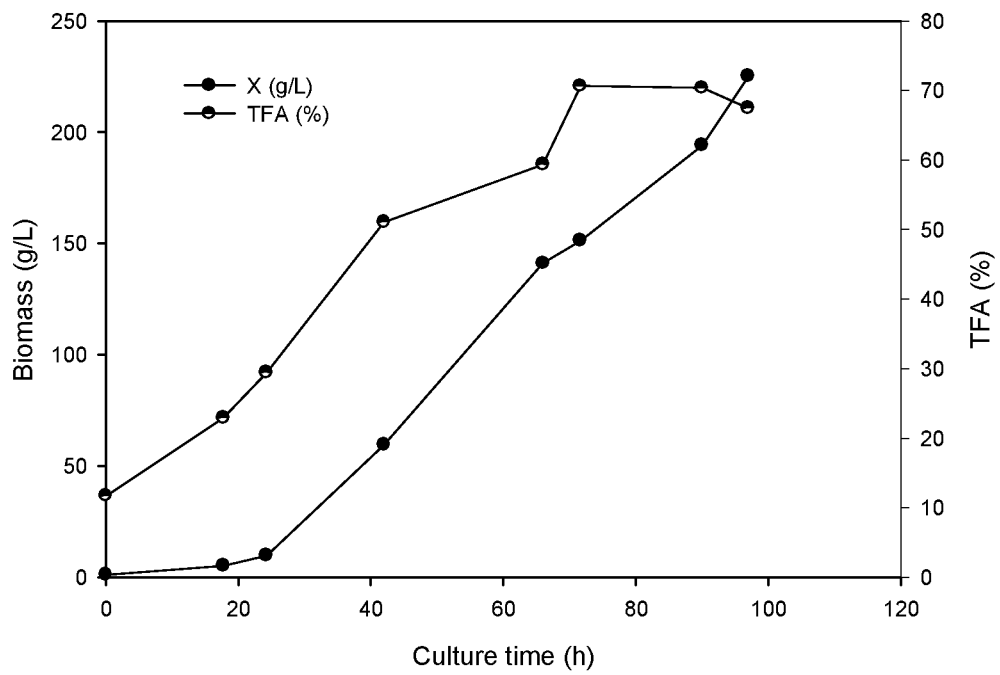
FIG. 1 is a graph showing the time profile of ONC-T18 cell concentration (biomass ("X")) and total fatty acid content (TFA %) during a 2 liter (L) fermentation.

Provided herein are methods for producing one or more polyunsaturated fatty acids. The methods include providing a microorganism capable of producing polyunsaturated fatty acids, providing a medium comprising a high concentration of one or more carbon sources, low pH, or both, and culturing the microorganism in the medium under sufficient conditions to produce the one or more polyunsaturated fatty acids. Optionally, the medium has a low pH. Optionally, the medium has a high concentration of one or more carbon sources. Optionally, the medium has a low pH and a high concentration of one or more carbon sources.

Also provided herein is a method of reducing contamination of a non-sterile culture comprising one or more microorganisms. The method includes culturing the microorganisms (i) in the presence of a high concentration of one or more carbon sources, (ii) under conditions of low pH, or (iii) a combination thereof, wherein the culturing reduces contamination of the non-sterile culture comprising the microorganisms. Optionally, the method comprises culturing the microorganisms in an open vessel. Optionally, the culturing comprises culturing the microorganisms in the presence of a high concentration of one or more carbon sources. Optionally, the culturing comprises culturing the microorganisms under conditions of low pH. Optionally, the culturing comprises culturing the microorganisms in the presence of a high concentration of one or more carbon sources and under conditions of low pH.

As used herein, the term "low pH" or "reduced pH" refers to a pH value lower than neutral pH. The term "low pH" generally refers to a pH value lower than 4.5. Optionally, low pH refers to a value of 2 to 4.5, inclusive, or any value between 2 and 4.5. Optionally, the pH is 3 to 3.5. It is understood that the pH of a culture may change over time, i.e., over the course of the fermentation process. As used herein, culturing the microorganism under conditions of low pH means that the pH of the culture or medium is monitored and adjusted over time to maintain the pH of the culture at low pH.

As used herein, the phrase "high concentration of a carbon source" refers to an amount of the carbon source of at least 200 g/L. For example, the concentration of the one or more carbon sources can be at least 200 g/L or greater than 200 g/L. Optionally, the concentration of the one or more carbon sources is 200 to 300 g/L. Optionally, the concentration of the one or more carbon sources is 200 to 250 g/L. It is understood that the concentration of a carbon source may change over time, i.e., over the course of the fermentation process. As used herein, a medium containing a high concentration of a carbon source means that the medium contains at least 200 g/L of the carbon source. As used herein, culturing the microorganism in a high concentration of a carbon source means that the initial concentration of the carbon source in the culture or medium is at least 200 g/L. As described in more detail below, the carbon source concentration can be monitored over time one or more times and once it reaches a certain threshold an additional amount of a carbon source can be added to the culture or medium. In this instance, the additional amount of the carbon source is a high concentration of a carbon source, i.e., at least 200 g/L of the carbon source.

Thus, provided is a method of culturing one or more microorganisms. The methods include culturing the microorganisms in a medium comprising a first amount of one or more carbon sources at a first concentration level, monitoring a carbon source concentration until the carbon source concentration is reduced below the first concentration level, and adding to the medium a second amount of one or more carbon sources to increase the carbon source concentration to a second concentration level. Optionally, the first and/or second concentration levels of the one or more carbon sources are greater than 200 g/L. Optionally, the second amount of the one or more carbon sources is added to the medium when the carbon source concentration level is reduced to 0 to 20 g/L. The provided methods can include repeated rounds of monitoring and additions of carbon sources as desired. Thus, the provided methods can include, after addition of the second amount of the one or more carbon sources, (a) culturing the microorganisms until the carbon source concentration of the one or more carbon sources is reduced below the second concentration level and (b) adding to the medium a third amount of one or more carbon sources to increase the carbon source concentration to a third concentration level. Optionally, the third concentration level of the one or more carbon sources is greater than 200 g/L. Optionally, the third amount of the one or more carbon sources is added to the medium when the carbon source concentration is reduced to 0 to 20 g/L. Optionally, the methods include, after addition of the third amount of the one or more carbon sources, (a) culturing the microorganisms until the carbon source concentration of the one or more carbon sources is reduced below the third concentration level and (b) adding to the medium a fourth amount of one or more carbon sources to increase the carbon source concentration to a fourth concentration level. Optionally, the fourth concentration level of the one or more carbon sources is greater than 200 g/L. Optionally, the fourth amount of the one or more carbon sources is added to the medium when the carbon source concentration is reduced to 0 to 20 g/L. Optionally, the one or more carbon sources in the first, second, third, and fourth amounts are the same.

In the provided methods, the carbon source concentration can be monitored one or more times. Optionally, the carbon source concentration can be monitored continuously (e.g., using a device that continuously monitors carbon source (e.g., glucose) concentrations in a medium) or periodically (e.g., by removing a sample of medium and testing carbon source concentration in the sample). Optionally, the carbon source concentration is monitored or determined before and/or after addition of an amount of the one or more carbon sources. Thus, for example, the provided methods can include monitoring the carbon source concentration one or more times between additions of the amounts of the one or more carbon sources. Optionally, the provided methods include monitoring or determining the carbon source concentration before addition of an amount of one or more carbon sources, after addition of an amount of one or more carbon sources and one or more times prior to addition of a further amount of one or more carbon sources. By way of example, the provided methods can include monitoring the carbon source concentration after addition of a first amount of the one or more carbon sources and, optionally, one or more times prior to addition of a second amount of the one or more carbon sources. The provided methods can include monitoring the carbon source concentration after addition of the second amount of the one or more carbon sources and, optionally, one or more times prior to addition of a third amount of the one or more carbon sources. The provided methods can include monitoring the carbon source concentration after addition of the third amount of the one or more carbon sources and, optionally, one or more times prior to addition of a fourth amount of the one or more carbon sources. Optionally, in the provided methods, the carbon source concentration is monitored once between each addition of the amounts of the one or more carbon sources. By way of example, the carbon source concentration is monitored after addition of the first amount of the one or more carbon sources and prior to addition of the second amount of the one or more carbon sources one time. Similarly, the carbon source concentration can be monitored after addition of the second amount of the one or more carbon sources and prior to addition of the third amount of the one or more carbon sources one time. Optionally, the carbon source concentration is monitored one time prior to addition of the second amount of the one or more carbon sources regardless of the number of further additions of amounts of the one or more carbon sources.

Carbon source concentration or levels can be monitored directly or indirectly by any means known to those of skill in the art. Optionally, the carbon source concentration is monitored by measuring dissolved oxygen levels, e.g., in the medium or in a sample from the medium. Optionally, the monitoring includes obtaining a sample of the medium and determining the carbon source concentration in the sample. Optionally, the step of determining the carbon source concentration comprises a colorimetric, enzyme-based, or fluorescence assay. Optionally, the step of determining carbon source concentration includes high pressure liquid chromatograph (HPLC).

I. Microorganisms

The methods described herein include extracting lipids from a population of microorganisms. The population of microorganisms described herein can be algae (e.g., microalgae), fungi (including yeast), bacteria, or protists. Optionally, the microorganism includes Thraustochytrids of the order Thraustochytriales, more specifically Thraustochytriales of the genus *Thraustochytrium*. Optionally, the population of microorganisms includes Thraustochytriales as described in U.S. Pat. Nos. 5,340,594 and 5,340,742, which are incorporated herein by reference in their entireties. The microorganism can be a *Thraustochytrium* species, such as the *Thraustochytrium* species deposited as ATCC Accession No. PTA-6245 (i.e., ONC-T18) as described in U.S. Pat. No. 8,163,515, which is incorporated by reference herein in its entirety. Thus, the microorganism can have an 18s rRNA sequence that is at least 95%, 96%, 97%, 98%, 99%, 99.1%, 99.2%, 99.3%, 99.4%, 99.5%, 99.6%, 99.7%, 99.8%, 99.9% or more (e.g., including 100%) identical to SEQ ID NO:1.

The microorganisms for use in the methods described herein can produce a variety of lipid compounds. As used herein, the term lipid includes phospholipids, free fatty acids, esters of fatty acids, triacylglycerols, sterols and sterol esters, carotenoids, xanthophyls (e.g., oxycarotenoids), hydrocarbons, and other lipids known to one of ordinary skill in the art. Optionally, the lipid compounds include unsaturated lipids. The unsaturated lipids can include polyunsaturated lipids (i.e., lipids containing at least 2 unsaturated carbon-carbon bonds, e.g., double bonds) or highly unsaturated lipids (i.e., lipids containing 4 or more unsaturated carbon-carbon bonds). Examples of unsaturated lipids include omega-3 and/or omega-6 polyunsaturated fatty acids, such as docosahexaenoic acid (i.e., DHA), eicosapentaenoic acid (i.e., EPA), and other naturally occurring unsaturated, polyunsaturated and highly unsaturated compounds.

II. Processes

Fermentation

The provided methods include or can be used in conjunction with additional steps for culturing microorganisms according to methods known in the art. For example, a Thraustochytrid, e.g., a *Thraustochytrium* sp., can be cultivated according to methods described in U.S. Patent Publication US 2009/0117194 or US 2012/0244584, which are herein incorporated by reference in their entireties. Microorganisms are grown in a growth medium (also known as "culture medium"). Any of a variety of medium can be suitable for use in culturing the microorganisms described herein. Optionally, the medium supplies various nutritional components, including a carbon source and a nitrogen source, for the microorganism.

Medium for Thraustochytrid culture can include any of a variety of carbon sources. Examples of carbon sources include fatty acids, lipids, glycerols, triglycerols, carbohydrates, polyols, amino sugars, and any kind of biomass or waste stream. Fatty acids include, for example, oleic acid. Carbohydrates include, but are not limited to, glucose, celluloses, hemicelluloses, fructose, dextrose, xylose, lactulose, galactose, maltotriose, maltose, lactose, glycogen, gelatin, starch (corn or wheat), acetate, m-inositol (e.g., derived from corn steep liquor), galacturonic acid (e.g., derived from pectin), L-fucose (e.g., derived from galactose), gentiobiose, glucosamine, alpha-D-glucose-1-phosphate (e.g., derived from glucose), cellobiose, dextrin, alpha-cyclodextrin (e.g., derived from starch), and sucrose (e.g., from molasses). Polyols include, but are not limited to, maltitol, erythritol, and adonitol. Amino sugars include, but are not limited to, N-acetyl-D-galactosamine, N-acetyl-D-glucosamine, and N-acetyl-beta-D-mannosamine. Optionally, the carbon source is glucose. As noted above, in the provided methods, the carbon source is provided at a high concentration, e.g., at least 200 g/L.

Optionally, the microorganisms provided herein are cultivated under conditions that increase biomass and/or production of a compound of interest (e.g., oil or total fatty acid (TFA) content). Thraustochytrids, for example, are typically cultured in saline medium. Optionally, Thraustochytrids can be cultured in medium having a salt concentration from about 2.0 g/L to about 50.0 g/L. Optionally, Thraustochytrids are cultured in medium having a salt concentration from about 2 g/L to about 35 g/L (e.g., from about 18 g/L to about 35 g/L). Optionally, the Thraustochytrids described herein can be grown in low salt conditions. For example, the Thraustochytrids can be cultured in a medium having a salt concentration from about 5 g/L to about 20 g/L (e.g., from about 5 g/L to about 15 g/L). The culture medium optionally include NaCl. Optionally, the medium include natural or artificial sea salt and/or artificial seawater.

The culture medium can include non-chloride-containing sodium salts (e.g., sodium sulfate) as a source of sodium. For example, a significant portion of the total sodium can be supplied by non-chloride salts such that less than about 100%, 75%, 50%, or 25% of the total sodium in culture medium is supplied by sodium chloride.

Optionally, the culture medium have chloride concentrations of less than about 3 g/L, 500 mg/L, 250 mg/L, or 120 mg/L. For example, culture medium for use in the provided methods can have chloride concentrations of between and including about 60 mg/L and 120 mg/L.

Examples of non-chloride sodium salts suitable for use in accordance with the present methods include, but are not limited to, soda ash (a mixture of sodium carbonate and sodium oxide), sodium carbonate, sodium bicarbonate, sodium sulfate, and mixtures thereof. See, e.g., U.S. Pat. Nos. 5,340,742 and 6,607,900, the entire contents of each of which are incorporated by reference herein.

Medium for Thraustochytrids culture can include any of a variety of nitrogen sources. Exemplary nitrogen sources include ammonium solutions (e.g., $NH_4$ in $H_2O$), ammonium or amine salts (e.g., $(NH_4)_2SO_4$, $(NH_4)_3PO_4$, $NH_4NO_3$, $NH_4OOCH_2CH_3$ ($NH_4Ac$)), peptone, tryptone, yeast extract, malt extract, fish meal, sodium glutamate, soy extract, casamino acids and distiller grains. Concentrations of nitrogen sources in suitable medium typically range between and including about 1 g/L and about 25 g/L.

The medium optionally include a phosphate, such as potassium phosphate or sodium-phosphate. Inorganic salts and trace nutrients in medium can include ammonium sulfate, sodium bicarbonate, sodium orthovanadate, potassium chromate, sodium molybdate, selenous acid, nickel sulfate, copper sulfate, zinc sulfate, cobalt chloride, iron chloride, manganese chloride calcium chloride, and EDTA. Vitamins such as pyridoxine hydrochloride, thiamine hydrochloride, calcium pantothenate, p-aminobenzoic acid, riboflavin, nicotinic acid, biotin, folic acid and vitamin B12 can be included.

The pH of the medium can be adjusted to between and including 3.0 and 10.0 using acid or base, where appropriate, and/or using the nitrogen source. Optionally, the medium is adjusted to a low pH as defined above. The medium can be sterilized.

Generally a medium used for culture of a microorganism is a liquid medium. However, the medium used for culture of a microorganism can be a solid medium. In addition to carbon and nitrogen sources as discussed herein, a solid medium can contain one or more components (e.g., agar or agarose) that provide structural support and/or allow the medium to be in solid form.

Cells can be cultivated for anywhere from 1 day to 60 days. Optionally, cultivation is carried out for 14 days or less, 13 days or less, 12 days or less, 11 days or less, 10 days or less, 9 days or less, 8 days or less, 7 days or less, 6 days or less, 5 days or less, 4 days or less, 3 days or less, 2 days or less, or 1 day or less. Cultivation is optionally carried out at temperatures from about 4° C. to about 30° C., e.g., from about 18° C. to about 28° C. Cultivation can include aeration-shaking culture, shaking culture, stationary culture, batch culture, semi-continuous culture, continuous culture, rolling batch culture, wave culture, or the like. Cultivation can be performed using a conventional agitation-fermenter, a bubble column fermenter (batch or continuous cultures), a wave fermenter, etc.

Cultures can be aerated by one or more of a variety of methods, including shaking. Optionally, shaking ranges from about 100 rpm to about 1000 rpm, e.g., from about 350 rpm to about 600 rpm or from about 100 to about 450 rpm. Optionally, the cultures are aerated using different shaking speeds during biomass-producing phases and during lipid-producing phases. Alternatively or additionally, shaking speeds can vary depending on the type of culture vessel (e.g., shape or size of flask).

Optionally, the level of dissolved oxygen (DO) is higher during the biomass production phase than it is during the lipid production phase. Thus, DO levels are reduced during the lipid production phase (i.e., the DO levels are less than the amount of dissolved oxygen in biomass production phase). Optionally, the level of dissolved oxygen is reduced below saturation. For example, the level of dissolved oxygen can be reduced to a very low, or even undetectable, level.

The production of desirable lipids can be enhanced by culturing cells according to methods that involve a shift of one or more culture conditions in order to obtain higher quantities of desirable compounds. Optionally, cells are cultured first under conditions that maximize biomass, followed by a shift of one or more culture conditions to conditions that favor lipid productivity. Conditions that are shifted can include oxygen concentration, C:N ratio, temperature, and combinations thereof. Optionally, a two-stage culture is performed in which a first stage favors biomass production (e.g., using conditions of high oxygen (e.g., generally or relative to the second stage), low C:N ratio, and ambient temperature), followed by a second stage that favors lipid production (e.g., in which oxygen is decreased, C:N ratio is increased, and temperature is decreased).

Pasteurization

Optionally, the resulting biomass is pasteurized to inactivate undesirable substances present in the biomass. For example, the biomass can be pasteurized to inactivate compound degrading substances. The biomass can be present in the fermentation medium or isolated from the fermentation medium for the pasteurization step. The pasteurization step can be performed by heating the biomass and/or fermentation medium to an elevated temperature. For example, the biomass and/or fermentation medium can be heated to a temperature from about and including 50° C. to about and including 95° C. (e.g., from about and including 55° C. to about and including 90° C. or from about and including 65° C. to about and including 80° C.). Optionally, the biomass and/or fermentation medium can be heated from about and including 30 minutes to about and including 120 minutes (e.g., from about and including 45 minutes to about and including 90 minutes, or from about and including 55 minutes to about and including 75 minutes). The pasteurization can be performed using a suitable heating means as known to those of skill in the art, such as by direct steam injection.

Optionally, a pasteurization step is not performed (i.e., the method lacks a pasteurization step.

Harvesting and Washing

Optionally, the biomass can be harvested according to methods known to those of skill in the art. For example, the biomass can optionally be collected from the fermentation medium using various conventional methods, such as centrifugation (e.g., solid-ejecting centrifuges) or filtration (e.g., cross-flow filtration) and can also include the use of a precipitation agent for the accelerated collection of cellular biomass (e.g., sodium phosphate or calcium chloride).

Optionally, the biomass is washed with water. Optionally, the biomass can be concentrated up to about and including 20% solids. For example, the biomass can be concentrated to about and including 5% to about and including 20% solids, from about and including 7.5% to about and including 15% solids, or from about and including 15% solids to about and including 20% solids, or any percentage within the recited ranges. Optionally, the biomass can be concentrated to about 20% solids or less, about 19% solids or less, about 18% solids or less, about 17% solids or less, about 16% solids or less, about 15% solids or less, about 14% solids or less, about 13% solids or less, about 12% solids or less, about 11% solids or less, about 10% solids or less, about 9% solids or less, about 8% solids or less, about 7% solids or less, about 6% solids or less, about 5% solids or less, about 4% solids or less, about 3% solids or less, about 2% solids or less, or about 1% solids or less.

Isolation and Extraction

The provided methods, optionally, include isolating the polyunsaturated fatty acids from the biomass or microorganisms using methods known to those of skill in the art. For example, methods of isolating polyunsaturated fatty acids are described in U.S. Pat. No. 8,163,515, which is incorporated by reference herein in its entirety. Optionally, the medium is not sterilized prior to isolation of the polyunsaturated fatty acids. Optionally, sterilization comprises an increase in temperature. Optionally, the polyunsaturated fatty acids produced by the microorganisms and isolated from the provided methods are medium chain fatty acids. Optionally, the one or more polyunsaturated fatty acids are selected from the group consisting of alpha linolenic acid, arachidonic acid, docosahexanenoic acid, docosapentaenoic acid, eicosapentaenoic acid, gamma-linolenic acid, linoleic acid, linolenic acid, and combinations thereof.

III. Products

Polyunsaturated fatty acids (PUFAs) and other lipids produced according to the method described herein can be utilized in any of a variety of applications, for example, exploiting their biological or nutritional properties. Optionally, the compounds can be used in pharmaceuticals, food supplements, animal feed additives, cosmetics, and the like. Optionally, the PUFAs and other lipids are used to produce fuel, e.g., biofuel. Lipids produced according to the methods described herein can also be used as intermediates in the production of other compounds.

Optionally, the lipids produced according to the methods described herein can be incorporated into a final product (e.g., a food or feed supplement, an infant formula, a pharmaceutical, a fuel, etc.) Suitable food or feed supplements for incorporating the lipids described herein into include beverages such as milk, water, sports drinks, energy drinks, teas, and juices; confections such as jellies and biscuits; fat-containing foods and beverages such as dairy products; processed food products such as soft rice (or porridge); infant formulae; breakfast cereals; or the like. Optionally, one or more produced lipids can be incorporated into a dietary supplement, such as, for example, a multivitamin. Optionally, a lipid produced according to the method described herein can be included in a dietary supplement and optionally can be directly incorporated into a component of food or feed (e.g., a food supplement).

Examples of feedstuffs into which lipids produced by the methods described herein can be incorporated include pet foods such as cat foods; dog foods and the like; feeds for aquarium fish, cultured fish or crustaceans, etc.; feed for farm-raised animals (including livestock and fish or crustaceans raised in aquaculture). Food or feed material into which the lipids produced according to the methods described herein can be incorporated is preferably palatable to the organism which is the intended recipient. This food or feed material can have any physical properties currently known for a food material (e.g., solid, liquid, soft).

Optionally, one or more of the produced compounds (e.g., PUFA) can be incorporated into a pharmaceutical. Examples of such pharmaceuticals include various types of tablets, capsules, drinkable agents, etc. Optionally, the pharmaceutical is suitable for topical application. Dosage forms can include, for example, capsules, oils, granula, granula subtilae, pulveres, tabellae, pilulae, trochisci, or the like.

The lipids produced according to the methods described herein can be incorporated into products as described herein by combinations with any of a variety of agents. For instance, such compounds can be combined with one or more binders or fillers. In some embodiments, products can include one or more chelating agents, pigments, salts, surfactants, moisturizers, viscosity modifiers, thickeners, emollients, fragrances, preservatives, etc., and combinations thereof.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

The examples below are intended to further illustrate certain aspects of the methods and compositions described herein, and are not intended to limit the scope of the claims.

EXAMPLES

Example 1. High Glucose Multi-Batch Fermentation of Microorganisms for Oil Production During our fermentation process development based on ONC-T18, the culture could survive extremely high concentration of glucose in the fermentation medium (up to 250 g/L). Such observation has led to development of fermentation processes with intentionally high initial glucose concentration and high glucose doses during the fermentation.

Thus, as described herein, unique oil fermentation processes for microorganisms was developed. Strategies including high initial concentration (up to 250 g/L) of glucose in the medium and high doses glucose supply during the fermentation were employed to achieve fast culture growth and oil production. Such carbon source supply strategy provides simpler yet highly efficient alternative to the continuous carbon feeding strategies employed by traditional fed-batch fermentation processes. The potential of foreign organism contamination was greatly reduced due to high osmotic pressure created by the high carbon substrate concentration. Such fermentation strategy was also applied to fermentations of a representative algal oil production strain, *Schizochytrium* sp. ATCC20888. However, no significant culture growth could be achieved under high glucose conditions. It was therefore demonstrated that it may be a unique trait of ONC-T18 as well as some other microorganisms in coping with such high concentration of carbon source.

High glucose fermentations of ONC-T18 were carried out at different fermentor scales with the same medium composition and glucose supply strategy. The fermentors used were 2 liter (L), 5 L, and 30 L with working volume of about 1.7 L, 4 L, and 25 L, respectively. Medium composition and glucose supply strategy are detailed in Table 1 below.

TABLE 1

Medium composition and glucose supply strategy during high glucose multi-batch fermentations of ONC-T18

|  |  | 2 L fermentor | 5 L fermentor | 30 L fermentor |
| --- | --- | --- | --- | --- |
| Initial volume |  | 1.3 L | 3.5 L | 25 L |
| Final volume |  | 1.7 L | 4.5 L | 25 L |
| Initial medium | Glucose | 242 g/L | 230 g/L | 204 g/L |
|  | Soy peptone | 2 g/L | 2 g/L | 2 g/L |
|  | MgSO4•7H2O | 4 g/L | 4 g/L | 4 g/L |
|  | FeCl3•6H2O | 0.005 g/L | 0.005 g/L | 0.005 g/L |
|  | Trace elements solution (stock) | 1.5 ml/L | 1.5 ml/L | 1.5 ml/L |
|  | KH2PO4 | 2.2 g/L | 2.2 g/L | 2.2 g/L |
|  | K2HPO4 | 2.4 g/L | 2.4 g/L | 2.4 g/L |

TABLE 1-continued

Medium composition and glucose supply strategy during high glucose multi-batch fermentations of ONC-T18

| | | 2 L fermentor | 5 L fermentor | 30 L fermentor |
|---|---|---|---|---|
| | (NH4)2SO4 | 20 g/L | 20 g/L | 20 g/L |
| | Vitamin solution (stock) | 3 g/L | 3 g/L | 3 g/L |
| | CaCl2•2H2O | 0.1 g/L | 0.1 g/L | 0.1 g/L |
| Base | 5M NaOH solution | | As needed | |
| Acid | 2M H2SO4 solution | | As needed | |
| Glucose supply during fermentation | | During the fermentation when glucose in the medium was near depletion, high dose of glucose was added to bring the aqueous glucose concentration to between 150 g/L and 250 g/L; no continuous glucose addition was made between each high dose of glucose | | |

Figure 2:
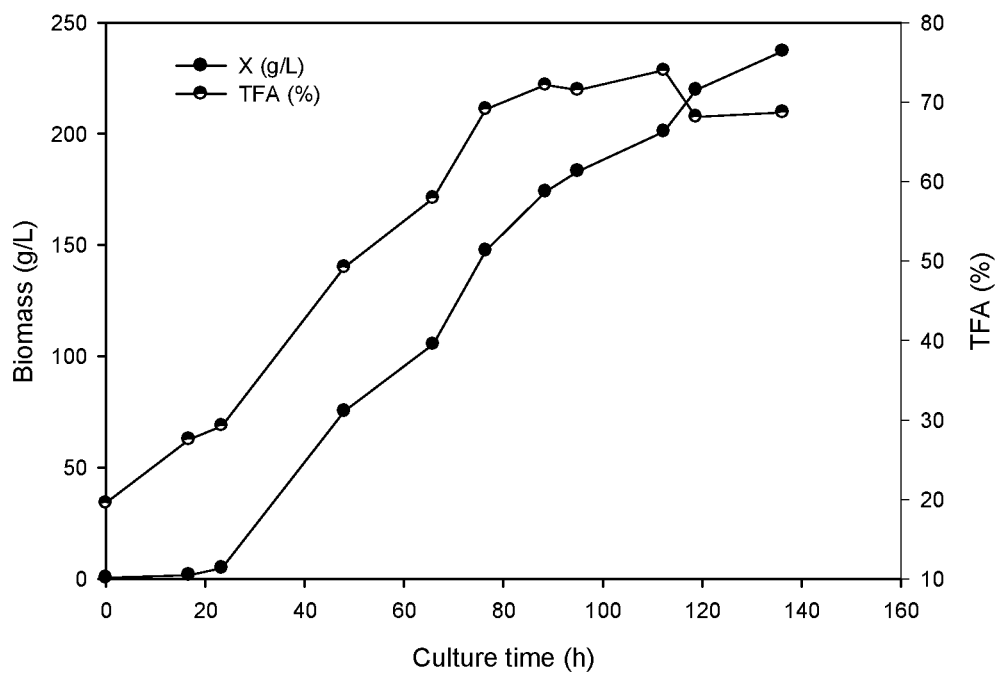
FIG. 2 is a graph showing the time profile of ONC-T18 cell concentration (biomass ("X")) and total fatty acid content (TFA %) during a 5 L fermentation.
Figure 3:
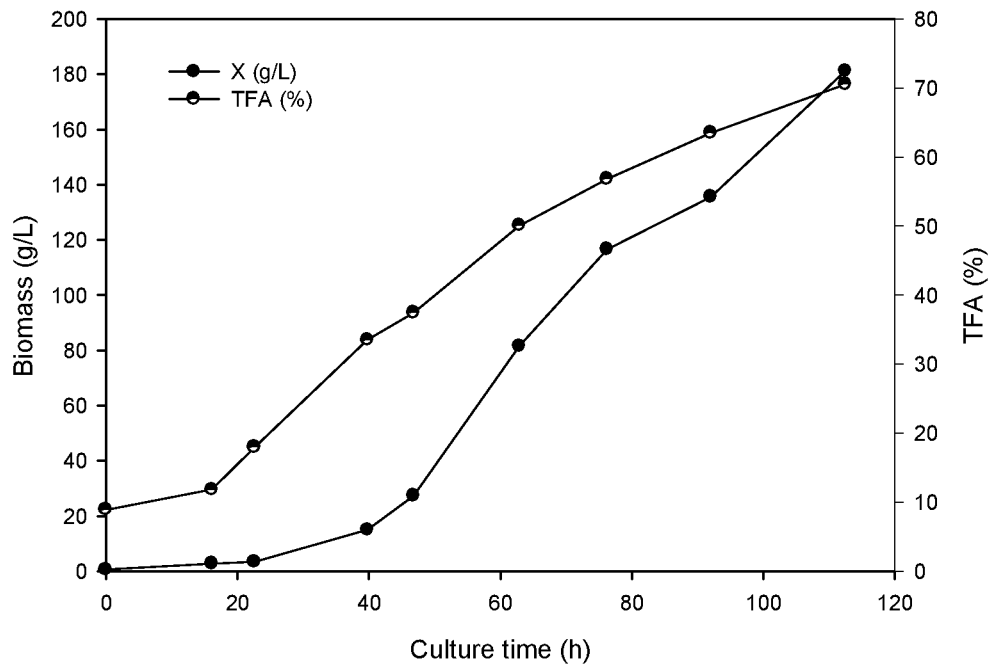
FIG. 3 is a graph showing the time profile of ONC-T18 cell concentration (biomass ("X")) and total fatty acid content (TFA %) during a 30 L fermentation.

FIGS. 1 to 3 are graphs showing the time profile of ONC-T18 cell concentration (biomass) and total fatty acid production (TFA %), using different scales of fermentors. Contrary to what has been reported on various microorganisms under high carbon concentrations, ONC-T18 was able to grow very fast under these harsh growth conditions and its biomass could increase up to 230 g/L during four to five days of fermentation. Final total fat content could reach 70% at all scales of fermentation tested, meeting or exceeding those reported in the literature for single cell oil fermentations.

Figure 4:
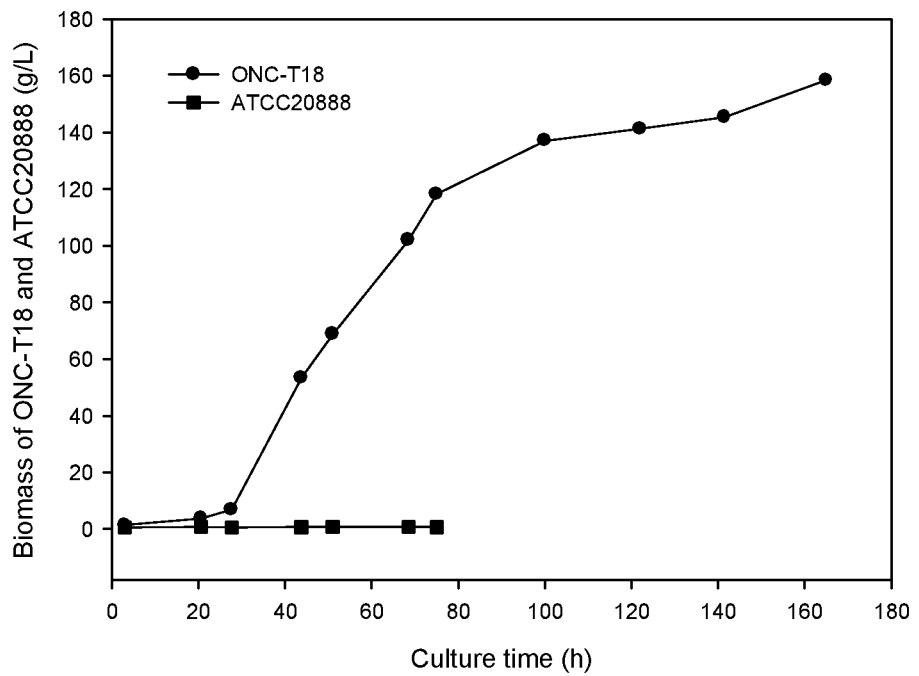
FIG. 4 is a graph showing the time profile of ONC-T18 and ATCC20888 cell concentration during parallel high glucose fermentations using the same fermentation medium formula (ONC formula).

To investigate whether the ability to grow and produce oil under high carbon concentrations is a unique trait of the strain ONC-T18 and highly related strains, a representative microalgae oil production strain *Schizochytrium* sp. ATCC20888 was used to run fermentations in parallel with ONC-T18. In the first parallel fermentation experiment, both strains were grown in 2 L fermentors using medium formula that were the same as those listed in Table 1, with the initial glucose concentration being 188 g/L in the ONC-T18 fermentor and 193 g/L in the ATCC20888 fermentor. No additional glucose was supplied into the ATCC20888 fermentor during the fermentation, as no significant consumption of the initial glucose had occurred. As demonstrated in FIG. 4, the strain *Schizochytrium* sp. ATCC20888 could not cope with such a high initial concentration of glucose in the medium and, therefore, had little growth in terms of total biomass.

Figure 5:
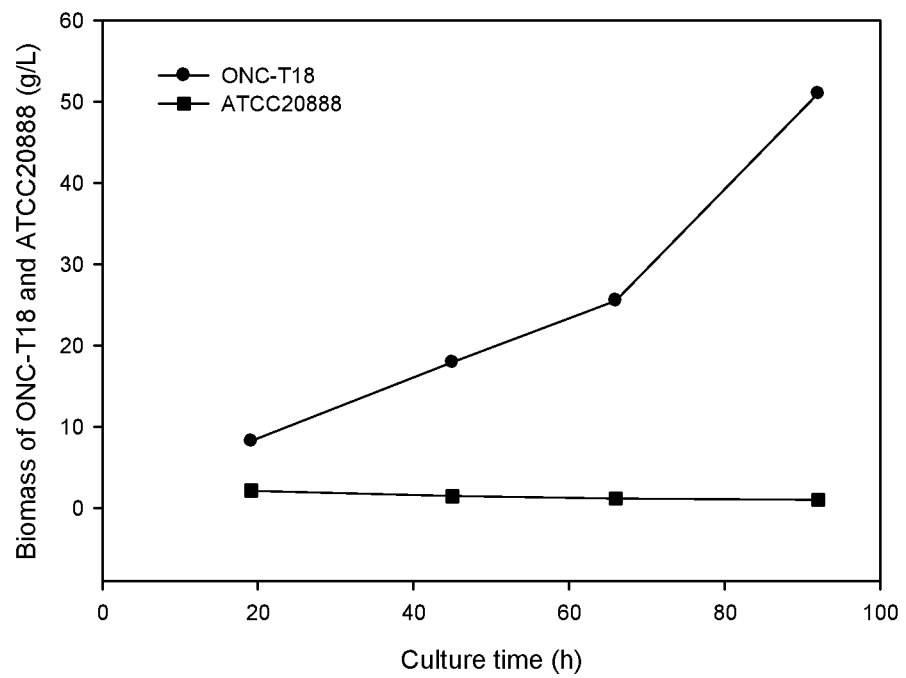
FIG. 5 is a graph showing the time profile of ONC-T18 and ATCC20888 cell concentration during parallel high glucose fermentations using the ONC fermentation medium formula for ONC-T18 and a different fermentation medium formula for ATCC20888.
Figure 6:
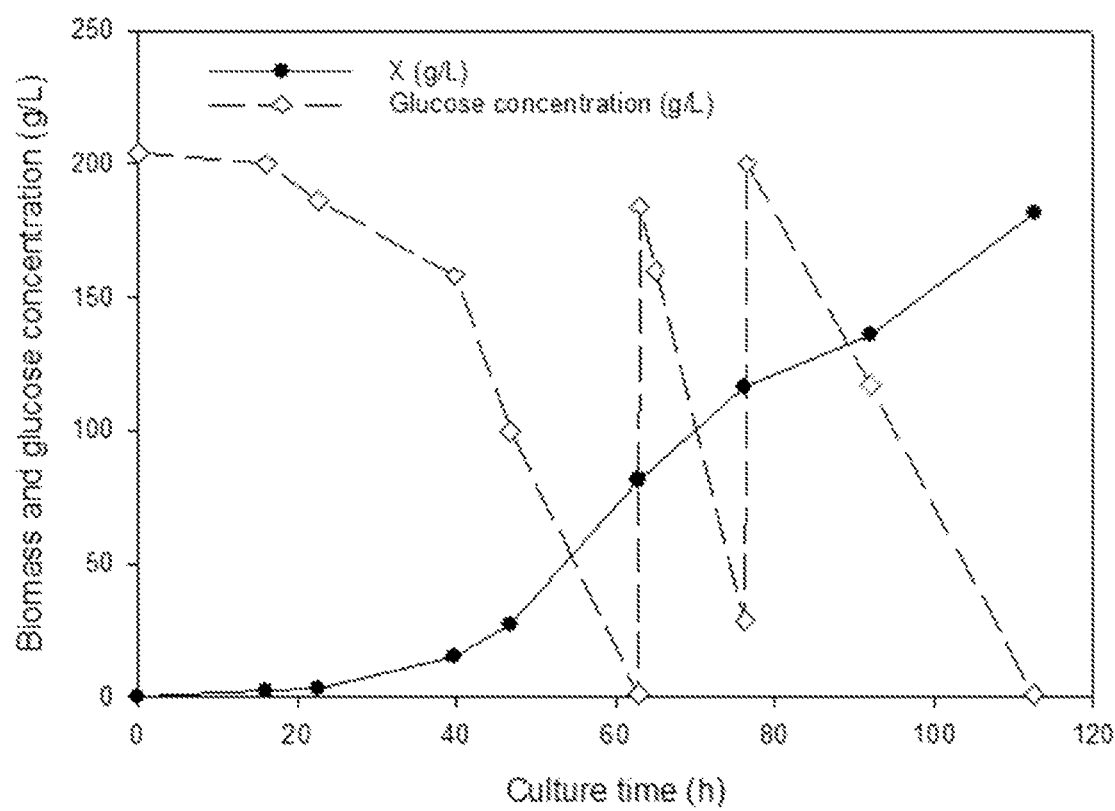
FIG. 6 is a graph showing the time profile of ONC-T18 cell concentration (biomass ("X")) and glucose concentration during a 30 L high glucose multi-batch fermentation.

To confirm that the inability of ATCC20888 to grow under high glucose condition was not due to the special composition of ONC's algal oil fermentation medium, another set of parallel fermentations were run in 2 L fermentors. During this experiment, ONC-T18 was still cultured using ONC's medium formula, while ATCC20888 was cultured using a medium formula adapted from US patent U.S. Pat. No. 6,607,900 to Bailey et al., which is incorporated by reference herein in its entirety. Due to time constraints, only initial glucose (258 g/L in the ONC-T18 fermentor and 211 g/L in the ATCC20888 fermentor) was provided and both fermentations were terminated before glucose was depleted (FIG. 5). Even with medium formula that was specifically developed for the strain ATCC20888, high initial glucose still presented too harsh a condition for the culture to grow significantly.

As has been demonstrated by fermentations above, the major difference between traditional fed-batch fermentation and the newly developed fermentation process was the high glucose concentration at the start and also during the course of the fermentation. The new process starts with about 200 g/L glucose (as compared to 60 g/L glucose of previous processes) and sufficient amounts of other nutrients (e.g., nitrogen in the form of ammonium sulfate, phosphorus in the form of potassium phosphate). Once the glucose is depleted or near depletion, as detected by a quick glucose assay of an off-line sample, another high dose of glucose is added at once to raise the glucose concentration in the fermentation medium back to around 200 g/L. Therefore, after each time of the high dose glucose addition, the fermentation was operated under high-glucose batch mode. Such cycles of glucose addition and batch operation is repeated until the oil production reaches the physiological limits of the culture, or the growth/production is limited by other fermentation conditions, such as dissolved oxygen supply, which is determined by the design factors of a particular fermentation system. Such a carbon supply strategy greatly simplifies the monitoring and control of algal oil fermentation process. This is evidenced by Table 2 showing the validation of this process at 2 L to 10 L. As shown in Table 2, with a 4 to 6 day cycle the biomass can reach 200 to 230 g/L with a total fatty acid content hitting about 70%.

TABLE 2

High glucose multi-batch strategy validation in 2 L to 10 L cultures.

| Batch # | Batch time | Biomass | TFA | MFA |
|---|---|---|---|---|
| 2011-2L-1 | 102 h | 227 g/L | 69% | 56% |
| | | 2.22 g/Lh | 156 g/L | 88 g/L |
| | | | 1.53 g/Lh | 0.86 g/Lh |
| 2011-5L-1 | 136 h | 237 g/L | 69% | 68% |
| | | 1.74 g/Lh | 163 g/L | 110 g/L |
| | | | 1.20 g/Lh | 0.81 g/Lh |
| 2012-10L-3 | 135 h | 193 g/L | 77% | 57% |
| | | 1.43 g/Lh | 149 g/L | 86 g/L |
| | | | 1.10 g/Lh | 0.63 g/Lh |
| 2012-10L-6 | 119 h | 191 g/L | 67% | 66% |
| | | 1.61 g/Lh | 128 g/L | 84 g/L |
| | | | 1.08 g/Lh | 0.71 g/Lh |
| 2012-10L-4 | 162 h | 227 g/L | 70% | 60% |
| | | 1.41 g/Lh | 159 g/L | 96 g/L |
| | | | 0.98 g/Lh | 0.59 g/Lh |

Another advantage of such high-glucose fermentation is the competitive edge presented by the high osmotic pressure, which few microorganisms are able to withstand resulting in less contamination. During two fermentations, additional glucose, other than the initial 200 g/L glucose, was added in a non-sterile form. No contamination was observed.

Example 2. Non-Sterile Fermentation Process for Culturing Microorganisms for Oil Production A significant cost to industrial scale fermentation includes those associated with sterilization. The costs include the expense of pressure vessel fermenters and steam-in-place systems as well as operating costs associated with generating steam. One way in which to reduce these costs is to ferment cultures under non-sterile conditions. However, non-sterile conditions are problematic for most microorganisms due to culture contamination, e.g., by bacteria.

In order to investigate non-sterile conditions in which ONC-T18 and similar microorganisms can grow, a medium without yeast extract or soya peptone was prepared. Table 3 lists the medium components. pH was controlled throughout the fermentation to 4.5 using sodium hydroxide (5N). The temperature was not controlled and a glucose feed of 75% was used during fermentation.

TABLE 3

Initial medium components. No other additions were made to the fermentation except NaOH and phosphoric acid to control pH.

| Ingredients | Amount (per liter) |
| --- | --- |
| Himedia Yeast Extract | 0 g/L |
| Himedia Soya Peptone | 0 g/L |
| Initial glucose | 60 g/L |
| NaCl | 9 g/L |
| Ammonium sulfate | 20 g/L |
| Monopotassium phosphate | 2 g/L |
| Magnesium sulfate | 4 g/L |
| Calcium chloride (solution) | 0.5 ml/L |
| FeCl3 6H2O (solution) | 0.5 ml/L |
| TES (solution) | 1.5 ml/L |
| Vitamin (solution) | 3 ml/L |

Air was supplied by a silicone tube with no sparger. The impeller was a Lightnin A310 style hydrofoil (axial flow). The open top vessel was a bottle with the top removed. The pH was controlled by the Sartorius PH control system on the Biostat B (Sartorius Corporation, Bohemia, N.Y.). There was no temperature control. The rate of fat accumulation over the duration of the fermentation was 0.5 g/L/h and the rate of DHA accumulation was 0.23 g/L/h. The results are shown in Table 4.

TABLE 4

Final results of open top fermentation.

| Time (hours) | Biomass (g/L) | Total Fatty Acids (g/L) | DHA (g/L) |
| --- | --- | --- | --- |
| 161.4 | 139 | 79 | 38 |

During a 500 L pilot scale run, bacterial contamination was detected at log hour 8. The contamination was determined by PCR to be in the genus *Bacillus*. The medium components are shown in Table 5.

TABLE 5

Medium components.

| Ingredients | Amount (per liter) |
| --- | --- |
| Himedia Soya Peptone | 10 g/L |
| Initial glucose | 60 g/L |
| NaCl | 9 g/L |
| Ammonium sulfate | 10 g/L |
| Potassium phosphate | 2.2 g/L |
| Potassium phosphate | 2.4 g/L |
| Magnesium sulfate | 4 g/L |
| Calcium chloride (solution) | 0.5 ml/L |
| FeCl3 6H2O (solution) | 0.5 ml/L |
| TES (solution) | 1.5 ml/L |
| Vitamin (solution) | 3 ml/L |

Figure 9:
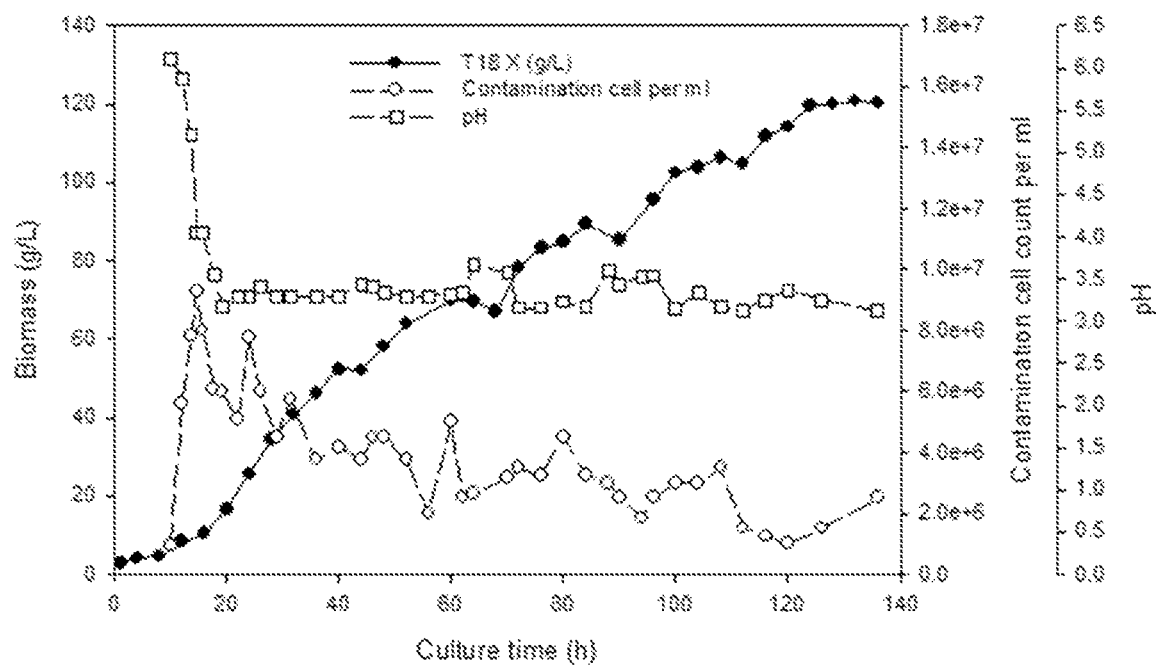
FIG. 9 is a graph showing reduced contamination of an ONC-T18 culture under low pH conditions.

The bacteria was counted using a hemocytometer, and its concentration calculated to the unit of cell count per ml of media. The bacteria population ceased to increase when the pH was dropped to 3.3. However, even at this low pH, the culture of ONC-T18 contained to grow as shown in FIG. 9. The results are shown in Table 6. It is noted that if this experiment were started at pH 3.3 instead of pH 6.5, no bacterial contamination would have been observed.

TABLE 6

Final results from fermentation assay.

| Time (hours) | Biomass (g/L) | Total Fatty Acids (g/L) | DHA (g/L) |
| --- | --- | --- | --- |
| 198 | 148 | 103 | 34 |

Figure 7:
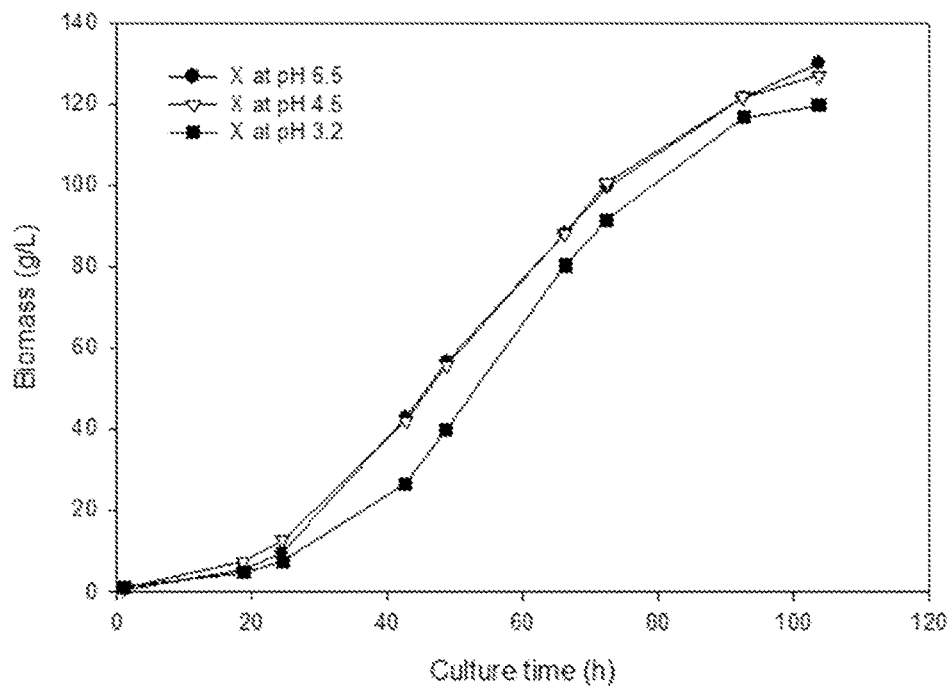
FIG. 7 is a graph showing the effect of pH on the growth of ONC-T18 under high glucose multi-batch fermentation conditions.
Figure 8:
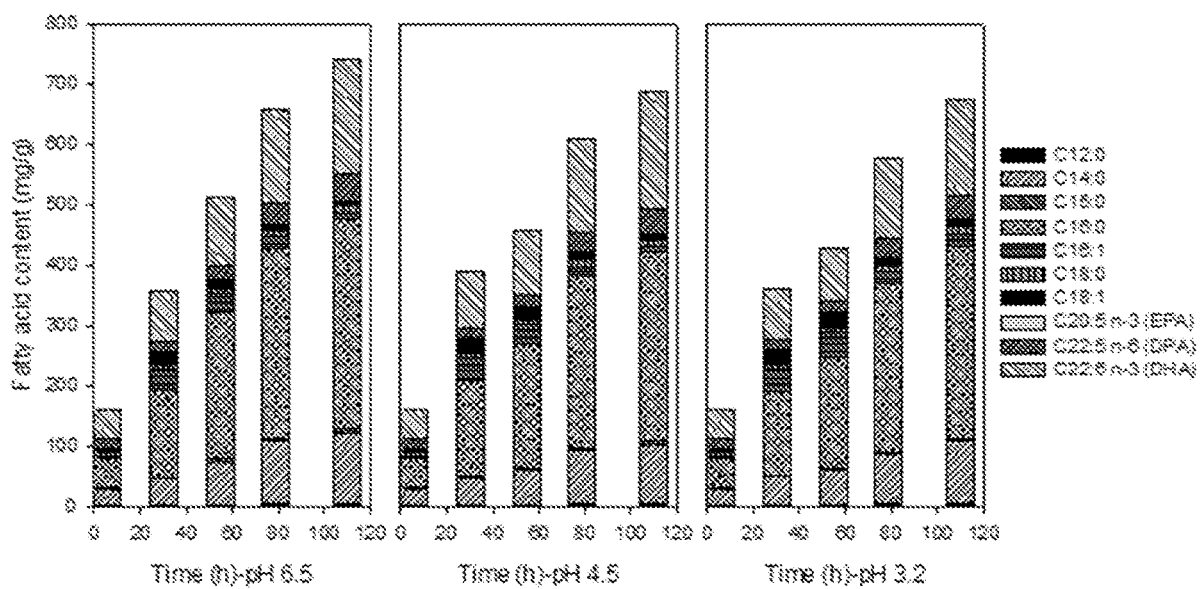
FIG. 8 is a graph showing the fatty acid profiles of ONC-T18 grown under different pH conditions and using high glucose multi-batch fermentation.

Different pH values were then tested for their effect on the microorganism, specifically, at pH values of 6.5, 4.5, and 3.2. ONC-T18 performed very well under even the very acidic condition. The results are shown in FIGS. 7 and 8. Fermentations for FIGS. 7 and 8 were carried out using high-glucose multi-batch feeding strategy as described in Example 1.

Thus, it is demonstrated herein that ONC-T18 and similar microorganisms can be fermented or grown under high stress conditions, e.g., high glucose (and thus high osmotic pressure) and/or low pH in order to reduce costs of oil production and reduce contamination.

What is claimed is:

1. A method for producing one or more polyunsaturated fatty acids, the method comprising:
   (a) providing a *Thraustochytrium* microorganism capable of producing polyunsaturated fatty acids;
   (b) providing a medium comprising one or more carbon sources at a first concentration level of greater than 200 g/L;
   (c) culturing the *Thraustochytrium* microorganism in the medium until the first concentration level of carbon sources is reduced to 0 to 20 g/L;
   (d) adding to the medium a second concentration of one or more carbon sources of greater than 200 g/L; and
   (e) culturing the *Thraustochytrium* microorganism in the medium under sufficient conditions to produce the one or more polyunsaturated fatty acids.

2. The method of claim 1, wherein the microorganism has ATCC Accession No. PTA-6245.

3. The method of claim 1, wherein the concentration of the one or more carbon sources in steps (b) and (d) is greater than 200 g/L to 250 g/L.

4. The method of claim 1, wherein the concentration of the one or more carbon sources in steps (b) and (d) is greater than 200 g/L to 300 g/L.

5. The method of claim 1, wherein the carbon source in steps (b) and (d) is selected from the group consisting of fatty acids, lipids, glycerols, triglycerols, carbohydrates, polyols, and amino sugars.

6. The method of claim 1, wherein the carbon source in steps (b) and (d) is glucose.

7. The method of claim 1, wherein the medium has a pH of 2 to 4.5.

8. The method of claim 1, wherein the medium has a pH of 3 to 3.5.

9. The method of claim 1, further comprising isolating the polyunsaturated fatty acids.

10. The method of claim 1, wherein the medium is not sterilized prior to isolation of the polyunsaturated fatty acids.

\* \* \* \* \*

SEQUENCE LISTING

<160> NUMBER OF SEQ ID NOS: 1

<210> SEQ ID NO 1
<211> LENGTH: 1723
<212> TYPE: DNA
<213> ORGANISM: Thraustochytrium sp.

<400> SEQUENCE: 1
gtagtcatac gctcgtctca aagattaagc catgcatgtg taagtataag cgattatact      60

-continued

```
gtgagactgc gaacggctca ttatatcagt tatgatttct tcggtatttt ctttatatgg    120
atacctgcag taattctgga attaatacat gctgagaggg cccgactgtt cgggagggcc    180
gcacttatta gagttgaagc caagtaagat ggtgagtcat gataattgag cagatcgctt    240
gtttggagcg atgaatcgtt tgagtttctg ccccatcagt tgtcgacggt agtgtattgg    300
actacggtga ctataacggg tgacggggag ttagggctcg actccggaga gggagcctga    360
gagacggcta ccacatccaa ggaaggcagc aggcgcgtaa attacccaat gtggactcca    420
cgaggtagtg acgagaaata tcaatgcggg gcgcttcgcg tcttgctatt ggaatgagag    480
caatgtaaaa ccctcatcga ggatcaactg gagggcaagt ctggtgccag cagccgcggt    540
aattccagct ccagaagcgt atgctaaagt tgttgcagtt aaaaagctcg tagttgaatt    600
tctggggcgg gagccccggt ctttgcgcga ctgcgctctg tttgccgagc ggctcctctg    660
ccatcctcgc ctcttttttt agtggcgtcg ttcactgtaa ttaaagcaga gtgttccaag    720
caggtcgtat gacctggatg tttattatgg gatgatcaga tagggctcgg gtgctatttt    780
gttggtttgc acatctgagt aatgatgaat aggaacagtt gggggtattc gtatttagga    840
gctagaggtg aaattcttgg atttccgaaa gacgaactac agcgaaggca tttaccaagc    900
atgttttcat taatcaagaa cgaaagtctg gggatcgaag atgattagat accatcgtag    960
tctagaccgt aaacgatgcc gacttgcgat tgcggggtgt ttgtattgga ccctcgcagc   1020
agcacatgag aaatcaaagt ctttgggttc cggggggagt atggtcgcaa ggctgaaact   1080
taaaggaatt gacggaaggg caccaccagg agtggagcct gcggcttaat ttgactcaac   1140
acgggaaaac ttaccaggtc cagacatagg taggattgac agattgagag ctctttcttg   1200
attctatggg tggtggtgca tggccgttct tagttggtgg agtgatttgt ctggttaatt   1260
ccgttaacga acgagacctc ggcctactaa atagcggtgg gtatggcgac atacttgcgt   1320
acgcttctta gagggacatg ttcggtatac gagcaggaag ttcgaggcaa taacaggtct   1380
gtgatgccct tagatgttct gggccgcacg cgcgctacac tgatgggttc aacgggtggt   1440
catcgttgtt cgcagcgagg tgctttgccg gaaggcatgg caaatccttt caacgcccat   1500
cgtgctgggg ctagattttt gcaattatta atctccaacg aggaattcct agtaaacgca   1560
agtcatcagc ttgcattgaa tacgtccctg ccctttgtac acaccgcccg tcgcacctac   1620
cgattgaacg gtccgatgaa accatgggat gacctttga gcgtttgttc gcagggggg    1680 tcagaactcg ggtgaatctt attgtttaga ggaaggtgaa gtc                     1723
```